United States Patent [19]

Kowalski

[11] Patent Number: 6,153,429

[45] Date of Patent: *Nov. 28, 2000

[54] CELL LINES USEFUL FOR IN VITRO ASSAY FOR INDENTIFICATION OF CARCINOGENS

[75] Inventor: Linda A. Kowalski, Vancouver, Canada

[73] Assignee: Vera Genics Ltd., Vancouver, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/951,983

[22] Filed: Oct. 16, 1997

Related U.S. Application Data

[63] Continuation-in-part of application No. 08/628,758, Apr. 5, 1996, Pat. No. 5,821,049.

[51] Int. Cl.⁷ .............................. C12N 5/06; C12N 5/08; C12N 5/10
[52] U.S. Cl. .................... 435/325; 435/354; 435/357; 435/366; 435/7.23
[58] Field of Search .................. 536/23.72; 435/7.23, 435/325, 352, 354, 362, 320.1, 69.1, 357, 366

[56] References Cited

U.S. PATENT DOCUMENTS

| | | | |
|---|---|---|---|
| 5,256,553 | 10/1993 | Overell | 435/172.2 |
| 5,273,880 | 12/1993 | Schiestl | 435/6 |
| 5,330,896 | 7/1994 | Billing | 435/7.23 |
| 5,336,613 | 8/1994 | Niwa et al. | 435/228 |
| 5,347,075 | 9/1994 | Sorge | 800/2 |
| 5,356,806 | 10/1994 | Harris et al. | 435/240.2 |
| 5,376,542 | 12/1994 | Schlegal | 435/172.2 |
| 5,382,510 | 1/1995 | Levine et al. | 435/6 |
| 5,387,508 | 2/1995 | Jaffe | 435/32 |
| 5,413,915 | 5/1995 | Case et al. | 435/25 |

FOREIGN PATENT DOCUMENTS 1292928  10/1991  Canada .

OTHER PUBLICATIONS

Fields et al. Virology. vol. 2. Second Ed. Raven Press, pp. 1634–1638, 1990.
Watts et al.I "Cellular transformation by human papillomavirus DNA in vitro" SCIENCE vol. 225, pp. 634–636, Aug. 10, 1984.
Petti et al. "Activation of the platelet–derived growth factor receptor by the bovine papillomavirus E5 tranforming protein" The EMBO Journal vol. 10. No. 4, pp. 845–855, 1991.
Yutsudo et al. "Functional dissociation of transforming genes of human papillomavirus type 16" Virology. vol. 166, pp. 594–597, 1988.
Leptak et al. "Tumorigenic transformation of murine keratinocytes by the E5 genes of bovine papillomasvirus type 1 and human papillomavirus type 16" J. of Virology. vol. 65. No. 12, pp. 7078–7083, Dec. 1991.
ATCC Catalogue of recombinant DNA materials, p. 40, 1993.
Amtmann et al., 1982, *Nature*, 296:675–677.
Casto et al., 1979, *Cancer Research*, 39:193–198.
Isfort et al., 1996, *Mutation Research*, 365:161–173.
Kowalski et al., 1992, *Cancer Lett.*, 64:83–90.
Stich et al., 1989, *Cancer Lett.*, 45:71–77.
Traul et al., 1979, *Int. J. Cancer*, 23:193–196.
Tsang et al., 1988, *Cancer Lett.*, 43:93–98.
Tsang et al., 1991, *Cancer Det. Prev.*, 15(5):423–427.

*Primary Examiner*—Donna Wortman
*Assistant Examiner*—Brenda G. Brumback
*Attorney, Agent, or Firm*—Sheridan Ross P.C.

[57] ABSTRACT

Disclosed test cells are useful for evaluating the carcinogenicity of a compound using a transformation assay. The test cell preferably is transfected with an oncogenic viral recombinant nucleic acid molecule encoding a transforming protein. Cell growth is scored to identify the presence or absence of a transformation characteristic, such as formation of foci, loss of growth factor or serum requirements or anchorage independence. The development of such a transformation characteristic indicates that the compound being tested is carcinogenic.

13 Claims, No Drawings

CELL LINES USEFUL FOR IN VITRO ASSAY FOR INDENTIFICATION OF CARCINOGENS

CROSS-REFERENCE TO RELATED APPLICATIONS

This application is a continuation-in-part of U.S. patent application Ser. No. 08/628,758, filed Apr. 5, 1996, now U.S. Pat. No. 5,821,049, issued Oct. 13, 1998 which is incorporated herein by reference in its entirety.

FIELD OF THE INVENTION

The present invention relates to recombinant molecules and cell lines useful in assays for the identification of carcinogenic compounds, and particularly transformation assays.

BACKGROUND OF THE INVENTION

New chemicals are constantly produced either for consumer use or as by-products into the environment. These potential human carcinogens are tested in cultures of prokaryotes or lower eukaryotes, in living rodents and in mammalian cells in tissue culture. Although these tests are reproducible, reliable, quick, relatively inexpensive and do not sacrifice higher animals, they are inadequate for testing human carcinogens.

Current assays rely on mutagenicity or genotoxicity to identify carcinogens because historically, only mutagens were believed to be carcinogens. Nevertheless, not all carcinogens are mutagens. Mutagenic carcinogens are usually electrophiles or capable of metabolic conversion to electrophiles which attack DNA causing base alteration and mutation. Nonmutagenic carcinogens induce cell proliferation and DNA synthesis by a variety of biochemical mechanisms eventually resulting in genome alteration; but they are not initially mutagenic. Some metal cations such as vanadate act as mitogens or alter protein phosphorylation. The International Agency for Research on Cancer (IARC) has identified twenty-three chemicals and groups of chemicals which are causally associated with cancer in humans. Of these, arsenic compounds, diethylstilbestrol and others are only weakly mutagenic.

Cell transformation assays can detect both mutagenic and nonmutagenic carcinogens. Therefore, presumably, a chemical that induces or promotes transformation is a carcinogen or tumor promoter. To investigate chemical carcinogenesis and mechanisms or transformation, several assays have been developed which rely on cell transformation. (See, e.g., DiPaolo, J. A. et al. (1969) "Quantitative Studies of in vitro Transformation by Chemical Carcinogens," *J. Natl. Cancer Inst.*, 42:867; Reznikoff, C. A. et al. (1973) "Establishment and Characterization of a Cloned Line of C3H Mouse Embryo Cells Sensitive to Postconfluence Inhibition of Cell Division," *Cancer Res.* 33:3231; Kakunaga, T. (1973) "A Quantitative System for Assay of Malignant Transformation by Chemical Carcinogens Using a Clone Derived from BALB/c3T3, " *Intl. J. Cancer*, 12:463). Transformed foci are the endpoint in these assays.

These tests, however, suffer from lack of reproducibility from laboratory to laboratory, technical difficulties, and difficulties in scoring foci as there are several different types of foci. Due to the low transformation frequency, large numbers of plates must be used to obtain statistically significant results for weak carcinogens. The C3H/10T½ assay requires six or more weeks of incubation before foci can be scored, increasing the loss of data due to contamination. Assays using cell transformation, nevertheless, respond to nongenotoxic carcinogens such as hormones and metals.

All virally-enhanced transformation assays have similar problems which compromise their usefulness. These include: variation in transformation frequency among various lots of cells, differing sensitivity to transfection and to carcinogens, variable rates of spontaneous transformation, technical complexity and limited commercial availability. Therefore, there exists a need for improved transformation assays and cell lines for use in such assays for rapid and reliable screening for carcinogens.

SUMMARY OF THE INVENTION

The present invention includes test cells suitable for use in such transformation assays to evaluate the carcinogenicity of a compound. The assay includes contacting a test cell with a compound being tested for carcinogenicity. The test cell is a test cell comprising a recombinant isolated nucleic acid molecule encoding a cellular transforming protein. The method further includes scoring cell growth of the test cell based on identification of transformation characteristics. A positive transformation characteristic indicates that the compound is carcinogenic. Transformation characteristics can include the formation of foci, loss of growth factor or serum requirements, or anchorage independence.

The cellular transforming proteins can be selected from the group of proteins having a function in or which initiate the mitotic cascade which causes transformation of cells from normal cells to cells having aberrant growth properties. In a further embodiment, the cellular transforming protein can be selected from growth factors, growth factor receptors, intracellular transducers, and nuclear transcription factors. The isolated nucleic acid molecule is preferably derived from a virus and in particular, an oncogenic virus, such as an oncogenic DNA virus or an oncogenic RNA virus. More particularly, the isolated nucleic acid molecule is preferably derived from a papilloma virus, such as a bovine papilloma virus (BPV). In particular, the isolated nucleic acid molecule can be derived from a BPV E5, E6 or E7 open reading frame.

Yet another embodiment of the present invention relates to a test cell for evaluating the carcinogenicity of a compound in an in vitro assay. Such a cell is transfected with an oncogenic viral recombinant nucleic acid molecule encoding a transforming protein. The test cell maintains a stable copy number of the recombinant nucleic acid molecule over at least about 5 passages of the test cell. In one embodiment, the oncogenic recombinant nucleic acid molecule does not include a portion of a viral genome which causes a variation in phenotypic transformation response to a carcinogen; instability of viral integration; variation of nucleic acid copy number; or variation or reduction in the ability of said test cell to be transformed by a carcinogen. Such a test cell can also be used in a method to evaluate the anticarcinogenicity of a compound.

In another embodiment of a test cell of the present invention, the oncogenic virus is an oncogenic DNA virus. Such an oncogenic DNA virus is preferably selected from the group of Papovaviruses, Herpesviruses, Hepadnaviruses, and Poxviruses. Such an oncogenic DNA virus is even more preferably selected from the group consisting of bovine papilloma virus type 1, bovine papilloma virus type 4, human papilloma viruses, cotton tail rabbit papilloma virus, polyoma viruses, Hamster polyoma virus, adenovirus and SV40. In yet another embodiment, the oncogenic virus is an oncogenic RNA virus. Such an oncogenic RNA virus is preferably selected from the group of mouse mammary tumor viruses (MMTV), human lymphotropic viruses, Rous sarcoma viruses, Rous-associated viruses, leukosis viruses (e.g., avian, murine (Moloney, Rauscher, Friend), rat, feline), reticuloendotheliosis viruses, pheasant viruses, murine sarcoma viruses, murine radiation leukemia viruses, murine endogenous viruses, primate sarcoma viruses, primate endogenous viruses, Mason-Pfizer monkey virus, human immunodeficiency viruses, Lentiviruses, and Foamy viruses. Even more preferably, such an oncogenic RNA virus is selected from the group of Simian sarcoma virus, McDonough feline sarcoma virus, Avian erythroblastosis virus, UR II avian sarcoma virus, Rous sarcoma virus, Yamaguchi avian sarcoma virus, Fujinami avian sarcoma virus, feline sarcoma virus, Abelson murine leukemia virus, Moloney murine sarcoma virus, Avian sarcoma virus, Kirsten murine sarcoma and Harvey murine sarcoma virus.

DETAILED DESCRIPTION

The present invention involves test cells for use in an in vitro assay for identifying compounds which are carcinogenic. The assay method of the present invention is a transformation assay. As such, the method involves contacting a cell of the present invention with a compound being tested for carcinogenicity and identifying whether the compound causes transformation of a cell having normal growth to a cell having abnormal or altered growth properties. Various aspects of transformed cells and identifying characteristics of transformation are discussed in more detail below.

A significant advantage of the present invention, because it involves a transformation assay, is that it is capable of identifying nongenotoxic carcinogens as well as genotoxic carcinogens. For example, the well-known Ames test only detects genotoxic carcinogens (i.e., mutagens). One option for identifying non-genotoxic carcinogens is by animal testing. However, animal testing is relatively expensive and time-consuming. Mutagenic carcinogens are usually electrophiles or are capable of metabolic conversion to electrophiles which attack DNA, causing base alteration and mutation. Non-genotoxic carcinogens induce cell proliferation and DNA synthesis by a variety of biochemical mechanisms eventually resulting in genome alteration; but they are not initially mutagenic. Non-genotoxic carcinogens can include metal cations such as vanadate, which act as mitogens or which alter protein phosphorylation.

The present invention provides many significant advantages over other known assays for identifying carcinogenic compounds and in particular, over other known transformation assays. Specifically, the present invention provides a test cell having an enhanced transformation response in the presence of carcinogens compared to normal or wild-type cells; provides cell lines with stable copy numbers of introduced nucleic acid molecules; provides cell lines which are genetically stable over repeated passaging; provides cell lines with uniform transformation frequency; has short incubation times; and has easily scored endpoints.

An important characteristic of the present invention is that the cells which form the basis for the assay have a recombinant isolated nucleic acid molecule that encodes a protein involved in the transformation of a cell. Such nucleic acid molecules are more particularly described below. That is, such proteins are involved in the transformation of normal cells to transformed cells. As used herein, a cell is considered to be transformed when, after it has been subjected to a carcinogenic agent in cell culture, it has developed aberrant growth properties or characteristics. Such transformation characteristics can include any properties associated with tumor or cancer cells. In particular, such characteristics can include formation of foci, loss of growth factor or serum requirements and/or anchorage independence. The presence of one or more of such transformation characteristics is indicative that the compound being tested is carcinogenic.

One transformation characteristic is when a cell, which normally does not form a focus, forms a focus when grown on a culture dish. Such cells, when not transformed, typically grow in a flat and organized pattern until they cover the surface of a Petri plate with liquid medium on top of them. Then, when each cell is touching its neighbor cell, cell growth stops by virtue of a phenomenon known as contact inhibition. Such cells, when transformed, are not contact inhibited and will grow to high densities in disorganized foci.

A further transformation characteristic which is indicative of a cell being transformed by a carcinogenic compound is cells becoming anchorage independent. When anchorage independence is the transformation characteristic being used in a particular assay, the cells used in the assay are cells which, when not transformed, are anchorage dependent. That is, when such cells are not transformed, they grow only when attached to a solid surface. Upon becoming transformed, such cells will grow in a medium without being attached to a solid surface.

A further transformation characteristic which is useful in assays of the present invention is the loss of growth factor or serum requirements. Cells used in assays of the present invention in which loss of growth factor or serum requirements is the transformation characteristic, when not transformed, require the presence of isolated growth factors or serum for growth. Upon transformation, such cells are able to grow in the absence of the growth factors or serum required by the untransformed cells.

The assay of the present invention includes contacting a test cell, such as a recombinant cell, with a compound being tested for carcinogenicity. For example, test cells can be grown in liquid culture medium or grown on solid medium in which the liquid medium or the solid medium contains the compound to be tested. In addition, the liquid or solid medium contains components necessary for cell growth, such as assimilable carbon, nitrogen and micro-nutrients. As used herein, a test cell can be a cell that has a recombinant isolated nucleic acid molecule that encodes a protein involved in the transformation of a cell. A cell, referred to herein as a recombinant cell, that has the above-mentioned recombinant isolated nucleic acid molecule includes a transfected cell, as well as the progeny of transfected cells, such as a cell that has stably integrated said nucleic acid molecule over generations of repeated cloning and selection (e.g., a subclone).

The assay involves contacting cells with the compound being tested for a sufficient time to allow for transformation of cells in the presence of carcinogenic compounds. The period of contact with the compound being tested can be either the entire growth phase of the assay prior to scoring or some smaller portion thereof. For example, it may be that for more toxic substances a shorter time of contact with the substance being tested is suitable. As used herein, the term "contact period" refers to the time period during which cells are in contact with the compound being tested. The term "incubation period" refers to the entire time during which cells are allowed to grow prior to scoring. Thus, the incubation period includes all of the contact period and may include a further time period during which the compound being tested is not present but during which growth is continuing prior to scoring.

After the incubation period, cell growth is scored for the presence or absence of one or more transformation indicators. The appearance of transformed cells in the present invention, as indicated by the presence of one or more transformation indicators, is considered to be indicative that the compound tested by the assay of the present invention is likely to be carcinogenic.

In the instance of the transformation characteristic being the formation of foci, cells can be stained and examined visually or with the aid of a microscope. The presence of foci on culture media indicates the presence of transformed cells. In a preferred embodiment of using foci formation as the transformation characteristic, test cells are grown with normal cells. As used herein, normal cells are "wild-type" cells, or cells that do not have identifying transformation characteristics as described above. In this manner, the normal cells will form a "lawn" or monolayer of contact inhibited cells. If the test compound is a carcinogen, each test cell will lose contact inhibition and grow to form a focus. If the test compound is non-carcinogenic, the test cells will be contact inhibited just as the normal cells on the lawn and only a monolayer of cells will be seen. This embodiment of the present invention provides several advantages. The normal cells function as "feeder" cells which condition the medium and metabolize the compound being tested. Further, the lawn of normal cells provides a background for comparison of transformed foci. Yet another advantage of the method is that all multi-layered aggregates of cells which overlay the lawn are counted as foci. In this embodiment, the ratio of normal cells to test cells can be between about 100:1 to about 1:1, more preferably from about 50:1 to 5:1, and most preferably about 10:1.

An identifying characteristic of test cell lines of the present invention is that when cultured in the presence of non-genotoxic carcinogens, such as mezerein, teleocidin, okadaic acid, arsenic, vanadate diethylstilbestrol, triethanolamine, clofibrate, di-2-ethylhexyl phthalate, p-dioxane, acetamide, thiourea, dieldrin, 1'-hydroxysafrole, safrole, 1-amino-H-1,2,4-triazole, and 12-O-tetradecanoylphorbol-13-acetate, the cells develop transformation characteristics, such as formation of foci, at a rate which is considered to be statistically significantly higher than the rate at which transformation characteristics are developed in the absence of non-genotoxic and genotoxic carcinogens. More preferably, such cells develop transformation characteristics in the presence of non-genotoxic carcinogens at a rate about 1 fold greater (i.e., 100% increase), more preferably about 25 fold greater, and most preferably about 50 fold greater than in the absence of non-genotoxic and genotoxic carcinogens.

In a further embodiment of the present invention, the occurrence of transformation characteristics is proportional to the carcinogenicity of the compound being tested. That is, the assay method quantifies the carcinogenicity of the compound being tested. In this manner, the relative carcinogenic potential of two different test compounds at a given concentration can be evaluated based on the relative occurrence of transformation characteristics.

As noted above, the present invention involves the use of a recombinant isolated nucleic acid molecule which encodes a protein involved in the transformation of cells. It is to be noted that the term "a" or "an" entity refers to one or more of that entity; for example, an isolated nucleic acid molecule refers to one or more isolated nucleic acid molecules or at least one nucleic acid molecule. As such, the terms "a" (or "an"), "one or more" and "at least one" can be used interchangeably herein. It is also to be noted that the terms "comprising", "including", and "having" can be used interchangeably. The term isolated nucleic acid molecule can include an isolated natural gene which encodes a protein involved in the transformation of a cell, such as a virally derived phosphorylating protein described in more detail below, or a homologue thereof, which is described in more detail below. A nucleic acid molecule of the present invention can include one or more regulatory regions, full-length or partial coding regions, or combinations thereof. The minimal size of a nucleic acid molecule of the present invention is the minimal size that encodes for a protein which is involved in the transformation of cells.

In accordance with the present invention, an isolated nucleic acid molecule is a nucleic acid molecule that has been removed from its natural milieu (i.e., that has been subject to human manipulation). For example, an isolated nucleic acid molecule can be a gene which has been separated from other genes with which it naturally occurs. As such, the term isolated does not reflect the extent to which the nucleic acid molecule has been purified. An isolated nucleic acid molecule can include DNA, RNA, or derivatives of either DNA or RNA.

An isolated nucleic acid molecule of the present invention can be obtained from its natural source either as an entire (i.e., complete) gene or a functional portion thereof. An isolated nucleic acid molecule can also be produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a protein which is involved in transformation of a cell.

A homologue of a nucleic acid molecule which encodes a protein involved in transformation of a cell can be produced using a number of methods known to those skilled in the art (see, for example, Sambrook et al., 1989, *Molecular Cloning: A Laboratory Manual*, Cold Spring Harbor Labs Press; and Watson et al., 1992, *Recombinant DNA*, Scientific American Books) The references Sambrook et al., ibid., and Watson et al., ibid., are incorporated by reference herein in their entireties. For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid. For example, to construct a nucleic acid molecule with a particular deletion, a plasmid containing a nucleic acid sequence can be linearized at a selected location by use of a restriction endonuclease and then digested with an exonuclease for various periods of time to generate nested sets of deletion mutants. The desired deletion mutant can be identified by standard sequence analysis or restriction mapping. The nucleic acid sequence having the desired deletion can then be recircularized or excised and ligated into a different vector. As another example, oligonucleotide-mediated mutagenesis can be used to create a more specific deletion. In this method, a mutagenic oligonucleotide is designed which contains a mismatched nucleotide sequence that will not hybridize with the sequence to be deleted, the mismatched sequence being flanked by a perfectly matched nucleotide sequence. The oligonucleotide is hybridized with the desired nucleic acid sequence, followed by an extension reaction to create a mutant copy of the original plasmid, with the mismatched portion "looped out".

An isolated nucleic acid molecule of the present invention can include a nucleic acid sequence that encodes at least one protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably. Proteins of the present invention include, but are not limited to, proteins having full-length naturally occurring coding regions, proteins having partial coding regions, fusion proteins, and combinations thereof.

Reference to a nucleic acid molecule which encodes a protein involved in the transformation of a cell refers to nucleic acid molecules that encode proteins which have a function in the mitotic cascade which causes transformation of cells from normal cells to cells having aberrant growth properties as described above or which have a function in initiation or activation of the mitotic cascade (e.g., proteins which control and sense cell-to-cell contact and communication, such as fibronectin receptors, gap junction proteins or transmembrane proteins, can lead to activation of the mitotic cascade). Such nucleic acid molecules can be currently known oncogenes or portions thereof, as well as oncogenes or portions thereof which are identified in the future. Such oncogenes can fall within any recognized class, but generally encode constituents of growth factor signal transduction pathways. While not expressly set forth herein, the present invention includes the use of nucleic acid sequences and molecules of known oncogenes by reference to published literature. For example, they can be genes which encode growth factors (e.g., sis), growth factor receptors (e.g., erbB, fms, trk), intracellular transducers (e.g., src, abl, raf, gsp, ras) or nuclear transcription factors (e.g., jun, fos, myc, erbA). Preferred constituents include intracellular transducers such as phosphorylating proteins, including tyrosine kinases and serine/threonine kinases.

In a preferred embodiment, a nucleic acid molecule of the present invention is virally derived. The nucleic acid molecule can be derived from an RNA or a DNA virus. In a preferred embodiment, the nucleic acid molecule can be derived from an oncogenic DNA or RNA virus.

According to the present invention, an oncogenic DNA virus is a DNA-containing virus which can transform a host cell through oncogenes that are either encoded in the viral DNA, or are encoded by the host DNA and activated by the virus. Some oncogenic DNA viruses can integrate into the host cell genome, although integration is not necessary for all oncogenic DNA viruses. Oncogenes in DNA viruses typically perform essential functions for the virus, such as replication of the viral DNA in the host cell. Oncogenic DNA viruses useful in the present invention include, but are not limited to, Papovaviruses (e.g., papilloma virus, polyoma virus, SV40), Herpesviruses (e.g., Epstein-Barr virus, cytomegalovirus), Hepadnaviruses (e.g., Hepatitis B virus), and Poxviruses (e.g., fibroma virus). Particularly preferred oncogenic DNA viruses useful in the present invention include bovine papilloma virus type 1 (BPV-1), bovine papilloma virus type 4 (BPV-4), human papilloma virus (HPV) (all strains), cotton tail rabbit papilloma virus (CRPV), polyoma virus, Hamster polyoma virus, adenovirus and SV40.

According to the present invention, an oncogenic RNA virus is an RNA-containing virus, preferably a retrovirus, which integrates into the host cell genome and which can transform a cell by activating a cellular proto-oncogene, for example, or by encoding an viral oncogene which results in transformation of the host cell. Oncogenic RNA viruses useful in the present invention include any member of the virus family Retroviridae, including, but not limited to, mouse mammary tumor viruses (MMTV), human lymphotropic viruses, Rous sarcoma viruses, Rous-associated viruses, leukosis viruses, reticuloendotheliosis viruses, pheasant viruses, murine sarcoma viruses, murine leukosis viruses (Moloney, Rauscher, Friend), murine radiation leukemia viruses, murine endogenous viruses, rat leukosis viruses, feline leukosis viruses, primate sarcoma viruses, primate endogenous viruses, Mason-Pfizer monkey virus, human immunodeficiency viruses, visna virus of sheep, and Foamy viruses. Particularly preferred oncogenic RNA viruses useful in the present invention include Simian sarcoma virus, McDonough feline sarcoma virus, Avian erythroblastosis virus, UR II avian sarcoma virus, Rous sarcoma virus, Yamaguchi avian sarcoma virus, Fujinami avian sarcoma virus, feline sarcoma virus, Abelson murine leukemia virus, Moloney murine sarcoma virus, Avian sarcoma virus, Kirsten murine sarcoma virus and Harvey murine sarcoma virus.

As used herein, a virally derived transforming protein can be any protein or group of proteins encoded by a viral genome that contributes to the transformation of a host cell. A viral genome may encode several different transforming proteins, one or more of which may be necessary to transform a host cell. In addition, a viral genome may encode a protein which regulates a host cell protooncogene such that the cellular protooncogene becomes an oncogene, leading to transformation of the host cell. More particularly, the virally derived transforming protein can be a protein involved with phosphorylation (e.g., regulates phosphorylation of a protein in the host cell). That is, the mechanism by which the protein transforms cells is by being involved in inappropriate phosphorylation. For example, such protein can be a kinase, which directly phosphorylates another molecule or a phosphatase which directly dephosphorylates another molecule. Alternatively, such a protein can bind to a receptor molecule, such as the PDGF receptor, thereby stimulating autophosphorylation.

In one embodiment, preferred isolated nucleic acid molecules of the present invention can be derived from papilloma viruses, particularly including human, cottontail rabbit and bovine papilloma viruses. More preferably, isolated nucleic acid molecules of the present invention are derived from bovine papilloma virus (BPV). Specifically, the E5, E6 and/or E7 papilloma virus ORFs (open reading frames), and particularly, the BPV E5, E6 and/or E7 ORFs are preferred, with the E5 and particularly, the BPV E5 ORF being most preferred. If the nucleic acid molecule is from bovine papilloma virus 4 (BPV-4), the E8 ORF is particularly preferred. If the nucleic acid molecule is from human papilloma virus, the E5, E6 and/or E7 ORFs are particularly preferred. If the nucleic acid molecule is from cottontail rabbit papilloma virus, the E6 and/or E7 ORFs are particularly preferred. It should be noted that in addition to these specific ORFs, such preferred isolated nucleic acid molecules of the present invention can also include other portions of viral genomes, including non-coding as well as coding regions or portions thereof.

In another embodiment, nucleic acid molecules of the present invention can be derived from other oncogenic DNA viruses, such as polyoma viruses. Particularly preferred nucleic acid molecules include the polyoma virus large T, mid-T and/or small T ORF. If the nucleic acid molecule is derived from Hamster polyoma virus, the large T ORF is particularly preferred. If the nucleic acid molecule is derived from SV40, the large T and/or the small T ORF are particularly preferred. When the nucleic acid molecule is derived from Hepatitis B virus, the X ORF is preferred. For Adenovirus, the ElA and/or E1B ORFs are preferred. In the instance where the nucleic acid molecule is derived from Epstein-Barr virus (Herpes), the EBNAII ORF is preferred. For HSV-2 (Herpes), preferred ORFs include MTR I, MTR II and/or MTR III.

If the nucleic acid molecule is derived from an oncogenic RNA virus, the following viruses and the corresponding ORFs within the genomes are particularly preferred, with the nucleic acid molecule ORF denoted in parentheses after the virus: Simian sarcoma virus (sis), McDonough feline sarcoma virus (fms), Avian erythroblastosis virus (erbB, erbA), UR II avian sarcoma virus (ros), Rous sarcoma virus (src), Yamaguchi avian sarcoma virus (yes), avian sarcoma virus (fps/fes), feline sarcoma virus (fps/fes), Abelson murine leukemia virus (abl), Moloney murine sarcoma virus (mos), Avian sarcoma virus (crk), Kirsten murine sarcoma (Ki-ras) and Harvey murine sarcoma virus (Ha-ras).

As discussed above, in addition to the above-mentioned specific ORFs, such preferred isolated nucleic acid molecules of the present invention can also include other portions of viral genomes, including non-coding as well as coding regions or portions thereof.

In a further embodiment, the isolated nucleic acid molecule can be a viral genome or a portion thereof from which portions of the genome have been deleted or inactivated by rearrangement, site-directed mutagenesis or other techniques. More particularly, it has now been recognized that significant advantages can be achieved by tailoring a viral genome for use in a transformation assay by removing portions which are implicated in causing: variation in phenotypic transformation response to a carcinogen; instability of viral integration; variation of nucleic acid copy number; or variation or reduction in the ability of a test cell to be transformed by a carcinogen. For example, virally derived nucleic acid molecules which do not include portions which are responsible for control of copy number, maintenance of the nucleic acid molecule as an episome, and/or integration into the cellular genome, are useful in the present invention.

Particular portions of a viral genome can be removed by any site-directed mutagenesis methods as described in detail above. Such methods are well known in the art. Alternatively, a test cell transfected with a recombinant viral genome having portions of the genome that have been deleted (i.e., removed) or made non-functional can be obtained by screening cells that were transfected with a wild-type genome for natural mutants which have the desired phenotype, without specifically targeting a particular nucleic acid sequence. Briefly, a preferred test cell of the present invention, in addition to having an enhanced transformation phenotype in the presence of a carcinogen compared to wild type cells, also maintains a stable copy number of recombinant nucleic acid molecule over at least 5 passages. This phenotype can be acquired by the loss of portions of the viral genome which affect integration, genetic stability and fluctuations in copy number, as discussed above. By cloning, subcloning and/or screening for a test cell having the desired phenotype, natural deletion mutants (e.g., viruses which may have deleted a portion of their genome upon integration into the host genome) are readily identified. Such a method is described in detail in the Examples section.

In the instance of nucleic acid molecules derived from papilloma viruses, nucleic acid molecules which do not have functional E1 and/or E2 ORFs (open reading frame) may be useful as nucleic acid molecules of the present invention. In the instance of nucleic acid molecules derived from human papilloma viruses, nucleic acid molecules which do not have functional E1 and/or E7 ORFs may be useful as nucleic acid molecules of the present invention. If a nucleic acid molecule is derived from polyoma viruses or SV40, nucleic acid molecules which do not have a portion of the large T ORF may be useful as nucleic acid molecules of the present invention. In the instance of Hamster polyoma virus, nucleic acid molecules which do not have a functional core origin replication may be useful as nucleic acid molecules of the present invention. In the case of Hepatitis B virus, nucleic acid molecules which do not have a functional C ORF may be useful as nucleic acid molecules of the present invention. For Adenoviruses, nucleic acid molecules which do not have a functional E2A ORF may be useful as nucleic acid molecules of the present invention. If an Epstein-Barr virus genome is used, nucleic acid molecules which do not have a functional EBNAI ORF may be useful as nucleic acid molecules of the present invention.

With reference to embodiments of the present invention in which nucleic acid molecules are described by reference to specific known genes, such as the src gene or the BPV E5 gene, such embodiments include not only the specific known molecules, but also nucleic acid molecules which are similar to the referenced genes to a large extent. For example, such nucleic acid molecules include nucleic acid molecules which hybridize with the referenced gene under stringent hybridization conditions. As used herein, stringent hybridization conditions refer to standard hybridization conditions under which nucleic acid molecules, including oligonucleotides, are used to identify molecules having similar nucleic acid sequences. Stringent hybridization conditions typically permit isolation of nucleic acid molecules having at least about 70% nucleic acid sequence identity with the nucleic acid molecule being used as a probe in the hybridization reaction. Such standard conditions are disclosed, for example, in Sambrook et al., ibid. Examples of such conditions include, but are not limited to, the following: Oligonucleotide probes of about 18–25 nucleotides in length with $T_m$'s ranging from about 50° C. to about 65° C., for example, can be hybridized to nucleic acid molecules typically immobilized on a filter (e.g., nitrocellulose filter) in a solution containing 5×SSPE, 1% Sarkosyl, 5×Denhardts and 0.1 mg/ml denatured salmon sperm DNA at 37° C. for about 2 to 12 hours. The filters are then washed 3 times in a wash solution containing 5×SSPE, 1% Sarkosyl at 37° C. for 15 minutes each. The filters can be further washed in a wash solution containing 2×SSPE, 1% Sarkosyl at 37° C. for 15 minutes per wash. Randomly primed DNA probes can be hybridized, for example, to nucleic acid molecules typically immobilized on a filter (e.g., nitrocellulose filter) in a solution containing 5×SSPE, 1% Sarkosyl, 0.5% Blotto (dried milk in water), and 0.1 mg/ml denatured salmon sperm DNA at 42° C. for about 2 to 12 hours. The filters are then washed 2 times in a wash solution containing 5×SSPE, 1% Sarkosyl at 42° C. for 15 minutes each, followed by 2 washes in a wash solution containing 2×SSPE, 1% Sarkosyl at 42° C. for 15 minutes each.

The present invention also includes a recombinant vector, which includes at least one isolated nucleic acid molecule of the present invention, inserted into any vector capable of delivering the nucleic acid molecule into a test cell. Such a vector contains heterologous nucleic acid sequences, that is nucleic acid sequences that are not naturally found adjacent to nucleic acid molecules of the present invention and that may be derived from a species other than the species from which the nucleic acid molecule(s) are derived. The vector can be either RNA or DNA, either prokaryotic or eukaryotic, and typically is a plasmid or a virus and preferably is a plasmid. One type of recombinant vector, referred to herein as a recombinant molecule and described in more detail below, can be used in the expression of nucleic acid molecules of the present invention.

Suitable and preferred nucleic acid molecules to include in recombinant vectors of the present invention are as generally disclosed herein for suitable and preferred nucleic acid molecules per se. Particularly preferred nucleic acid molecules to include in recombinant vectors, and particularly in recombinant molecules, of the present invention include BPV E5, BPV E6, BPV E7, BPV-4 E8, CRPV E6, CRPV E7, HPV E5, HPV E6, and HPV E7 from any strain of BPV or HPV, respectively. Additional preferred nucleic acid molecules to include in recombinant vectors, and particularly in recombinant molecules, of the present invention include viral derived nucleic acid molecules encoding any of the heretofore mentioned open reading frames (ORFs) as described above.

A preferred vector of the present invention is identified as plasmid pJS55 which is reported by Sparkowski et al., (1994) "Mutation of the Bovine Papilloma Virus E5 Oncoprotein at Amino Acid 17 Generates Both High- and Low-Transforming Variants", *J. Virol.*, 68:6120–6123, which is incorporated herein by reference in its entirety. Another preferred vector of the present invention is identified as plasmid pdBPV-1 (142-6) which is reported by Sarver, et al. (1982) "Transformation and Replication in Mouse Cells of a Bovine Papillomavirus-pML2d Plasmid Vector That can be Rescued in Bacteria.", *Proc. Natl. Acad. Sci. (USA)* 79:7147–7151, which is incorporated herein by reference in its entirety. pdBPV-1 (142-6) contains the complete BPV-1 genome cloned into the plasmid pML2d at the Bam HI site.

In the present assay, an isolated nucleic acid molecule which encodes a protein involved in the transformation of cells is expressed by culturing a transfected cell capable of expressing the protein under conditions effective to produce the protein. A preferred cell to culture is a recombinant cell that is capable of expressing the protein, the recombinant cell being produced by transfecting a host cell with one or more nucleic acid molecules of the present invention. It should be noted that such a recombinant cell may be repeatedly cloned and selected until such nucleic acid molecule or molecules have stably integrated into the host cell genome. Transfection of a nucleic acid molecule into a cell can be accomplished by any method by which a nucleic acid molecule can be inserted into the cell. Transfection techniques include, but are not limited to, electroporation, $CaCl_2$ precipitation, microinjection, lipofection, adsorption, and protoplast fusion. Suitable and preferred nucleic acid molecules with which to transform a cell are as disclosed herein for suitable and preferred nucleic acid molecules per se. Particularly preferred nucleic acid molecules to include in recombinant cells of the present invention include BPV E5, BPV E6, BPV E7, HPV E5, HPV E6, and HPV E7 from any strain of BPV or HPV, respectively. Additional preferred nucleic acid molecules to include in recombinant cells of the present invention include oncogenic viral nucleic acid molecules encoding any of the heretofore mentioned open reading frames.

Transfected nucleic acid molecules of the present invention can remain extrachromosomal or can integrate into one or more sites within a chromosome of the transfected (i.e., recombinant) cell in such a manner that their ability to be expressed is retained. Preferably, once a host cell of the present invention is transfected with a nucleic acid molecule of the present invention, the nucleic acid molecule is integrated into the host cell genome. A significant advantage of integration is that the nucleic acid molecule is stably maintained in the cell. The nucleic acid molecule can be integrated into the genome of the host cell either by random or targeted integration.

Suitable host cells to transfect include any cell that can be transfected with a nucleic acid molecule of the present invention, including mammalian, avian and herptile, and, preferably, the host cells are mammalian. Host cells can be either untransfected cells or cells that are already transfected with at least one nucleic acid molecule. Host cells of the present invention can be any cell capable of expressing at least one protein of the present invention. Preferred host cells include any mammalian cell, and more particularly, adherent cells which are normally contact-inhibited (i.e., contact-inhibited as a non-transformed cell), such as fibroblasts, keratinocytes, and established fibroblast and epithelial cell lines. Particularly preferred host cells include mouse C127 cells, human newborn foreskin keratinocytes, primary fibroblast cultures of C57BL/6J mice, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, Vero cells, C3H/10T½ cells, and BALB/c3T3 cells. Most preferred host cells include mouse C127 cells, C3H/10T½ cells, human newborn foreskin keratinocytes and primary fibroblast cultures of C57BL/6J mice. Additional appropriate mammalian host cells include other kidney cell lines, other fibroblast cell lines (e.g., human, murine or chicken embryo fibroblast cell lines), myeloma cell lines, Chinese hamster ovary cells, mouse NIH/3T3 cells, $LMTK^{31}$ cells and/or HeLa cells.

A recombinant cell is preferably produced by transfecting a host cell with one or more recombinant molecules, each comprising one or more nucleic acid molecules of the present invention operatively linked to an expression vector containing one or more transcription control sequences. The phrase, operatively linked, refers to insertion of a nucleic acid molecule into an expression vector in a manner such that the molecule is able to be expressed when transfected into a host cell. As used herein, an expression vector is a DNA or RNA vector that is capable of transfecting a host cell and of effecting expression of a specified nucleic acid molecule. Preferably, the expression vector is also capable of replicating within the host cell. Expression vectors can be either prokaryotic or eukaryotic, and are typically plasmids. Expression vectors of the present invention include any vectors that function (i.e., direct gene expression) in recombinant cells of the present invention, including in mammalian cells.

Recombinant molecules of the present invention may also (a) contain secretory signals (i.e., signal segment nucleic acid sequences) to enable an expressed protein of the present invention to be secreted from the cell that produces the protein and/or (b) contain fusion sequences which lead to the expression of nucleic acid molecules of the present invention as fusion proteins. Recombinant molecules may include intervening and/or untranslated sequences surrounding and/ or within the nucleic acid sequences of nucleic acid molecules of the present invention.

Suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments.

Nucleic acid molecules of the present invention can be operatively linked to expression vectors containing regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. In one embodiment, such transcription control sequences can be derived from the same source as the isolated nucleic acid molecule. For example, if the nucleic acid molecule is virally derived or particularly derived from BPV, a suitable transcription control sequence can be virally derived or derived from BPV, respectively. For example, the BPV E2 ORF encodes a protein which stimulates an enhancer and may be a suitable transcription control sequence. Preferred transcription control sequences include those which function in mammalian cells. Such sequences include, but are not limited to, bacteriophage T7 promoter, bacteriophage T3 promoter, metallothionein, promoters of various antibiotic resistance genes, herpesvirus promoters, adenovirus promoters, cytomegalovirus promoters, simian virus 40 promoter, and Rous sarcoma virus promoter.

Transcription control sequences of the present invention can also include naturally occurring transcription control sequences naturally associated with a nucleic acid molecule of the present invention prior to isolation.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transfected, examples of which are disclosed herein.

A recombinant cell of the present invention includes any cell transfected with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transfected with one or more recombinant molecules including nucleic acid molecules encoding one or more proteins of the present invention. In this manner, a transfected cell of the present invention can be transfected with nucleic acid molecules encoding proteins involved in cell transformation through more than one mechanism of cell transformation. For example, a cell of the present invention can be transfected with a nucleic acid molecule which encodes for a phosphorylating protein and for a transcription factor. Such a transfected cell may be either more sensitive to transformation by a potential carcinogen or sensitive to transformation by potential carcinogens which function by different mechanisms or both.

A further embodiment of the present invention includes a test cell of the present invention in which the cellular genome has been further modified to increase the susceptibility of the test cell to transformation by a recombinant oncogenic viral nucleic acid molecule as described herein. As used herein, such a modification of the cellular genome can include a modification (e.g., deletion, insertion, mutation) of a portion or portions of the test cell's native genome in such a way as to make the test cell more susceptible to transformation. For example, a test cell having a modified genome can have a defect in a cellular mechanism which normally protects a cell from becoming transformed. Such a defect includes a defect in a DNA damage repair mechanism, a defect in cell cycle control, and/or a defect in the ability to prevent damage induced by oxygen free radicals. Such defects and cells having such defects are described in detail in copending U.S. application Ser. No. 08/696,695, filed Aug. 14, 1996, which is incorporated herein by reference in its entirety. For example, a human test cell transfected with a human papilloma virus (HPV) nucleic acid molecule can also have a deletion of the DCC tumor suppressor gene in the test cell genome. Normally, the presence of the DCC gene may suppress the phenotypic expression of the HPV-transformation of the test cell. If a portion or all of the DCC tumor gene is mutated or deleted such that the DCC gene is rendered non-functional, then the HPV-transfected cell becomes more susceptible to transformation. Modification of a test cell genome can be accomplished by methods that include, but are not limited to, selective or directed mutation of the above-mentioned portion or portions of the test cell genome or classical genetic selection of naturally occurring mutations. Such methods have been previously described herein.

It will be appreciated by one skilled in the art that use of recombinant DNA technologies can improve control of expression of transfected nucleic acid molecules by manipulating, for example, the number of copies of the nucleic acid molecules within a test cell, the efficiency with which those nucleic acid molecules are transcribed, the efficiency with which the resultant transcripts are translated, and the efficiency of post-translational modifications. Recombinant techniques useful for controlling the expression of nucleic acid molecules of the present invention include, but are not limited to, integration of the nucleic acid molecules into one or more test cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the test cell, and deletion of sequences that destabilize transcripts. The activity of an expressed recombinant protein of the present invention may be improved by fragmenting, modifying, or derivatizing nucleic acid molecules encoding such a protein.

In accordance with the present assay, recombinant cells of the present invention are seeded on a culture dish in medium under conditions which promote cell growth and expression of a protein involved in the transformation of cells and in the presence of a compound being tested for carcinogenicity. Effective conditions include, but are not limited to, appropriate media, temperature, pH and oxygen conditions that permit cell growth. An appropriate, or effective, medium refers to any medium in which a cell of the present invention, when cultured, is capable of cell growth and expression of nucleic acid molecules of the present invention. Such a medium is typically a solid or liquid medium comprising growth factors and assimilable carbon, nitrogen and phosphate sources, as well as appropriate salts, minerals, metals and other nutrients, such as vitamins. Culturing is typically conducted in petri plates. Culturing is carried out at a temperature, pH and oxygen content appropriate for the recombinant cell. Such culturing conditions are within the expertise of one of ordinary skill in the art.

Preferably, culturing conditions are adjusted to eliminate conditions conducive to redox activity to avoid toxicity problems or false positive reactions due to the generation of peroxides and active oxygen free radicals in the culture. For example, the present inventors have discovered that if contaminating peroxides are present in the solvent tetrahydrofuran, when the solvent is used with a compound having redox activity, the combination in culture can result in cell toxicity. Additionally, enhanced transformation in cultures exposed to the nongenotoxic metal salt, $Fe(III)Cl_3$, may occur by a similar mechanism since $Fe^{+3}$ may be redox active. This result indicates that potentially redox active compounds may produce inaccurate results if conditions exist to facilitate redox activity. These results are discussed in more detail in Example 5 below.

The incubation time for growth of cells can vary but is sufficient to allow for the development of transformation characteristics in transformed cells. It will be recognized that shorter incubation times are preferable because compounds can be more rapidly screened for carcinogenicity. In this regard, cell lines of the present invention, under appropriate growth conditions, will develop transformation characteristics in the presence of non-genotoxic carcinogens in less than about 21 days, more preferably less than about 14 days, and even more preferably less than about 10 days.

A further aspect of cell lines of the present invention is that the copy number of the isolated nucleic acid molecule which encodes a protein involved in the transformation of a cell which is transfected into a cell is stable. A significant problem associated with prior known transformation assays is that the viral copy number, in the instance of use of a virally derived protein, can fluctuate wildly. Thus, the ability of such assays to maintain a uniform transformation response after repeated passaging is impaired. In contrast, the present assay involves use of cell lines with stable copy numbers of transfected nucleic acid molecules. In particular, the copy number of transfected nucleic acid molecules in cells of the present invention is typically sufficient to achieve adequate production of the encoded protein. If the nucleic acid molecule is well expressed, the copy number can be as low as one. More preferably, the copy number is typically between about 100 and about 200. Reference to "stable copy number" herein means the copy number remains preferably within at least about 50% of the original copy number over the total number of passages, and more preferably within at least about 25% of the original copy number, and even more preferably, within at least about 10% of the original copy number. The desired copy numbers can be maintained over 5 or more passages of the cell line, and preferably over 10 or more passages, and more preferably over 50 or more passages.

Test cells of the present invention having the above-described genotypes and phenotypes can be produced and selected using techniques known in the art. Such techniques have been described in detail herein. In particular, it should be noted that suitable test cells are typically highly selected by cloning and subcloning cells transfected with a recombinant nucleic acid molecule as described herein. Such selection techniques, as discussed in detail in the Examples section, allow production and identification of a test cell which is reliably useful in the transformation assays of the present invention.

A further aspect of the present invention is a method to identify anti-carcinogenic agents. This method can use materials as described generally herein for other methods of the present invention. The method to identify anti-carcinogenic agents (i.e., transformation inhibitors) can involve the use of test cells which comprise an isolated nucleic acid molecule which encodes a protein involved in the transformation of a cell, as is described in detail above. In one embodiment, this method includes contacting such a test cell with a known carcinogen. Such a carcinogen can be either a mutagenic or nonmutagenic carcinogen and preferably is a nonmutagenic carcinogen. As used herein, the term "carcinogen" is a compound which causes a cell to demonstrate transformation characteristics in a transformation assay of the present invention. This method further includes contacting such a test cell in the presence of a carcinogen with a compound to be evaluated for its effectiveness as an anti-carcinogenic agent. Such a cell is contacted with both a carcinogen and a compound to be tested in the manner as noted above for other methods of the present invention. After a suitable incubation period, cell growth is scored for the presence or absence of one or more transformation indicators as noted above.

In another embodiment of the method to identify anticarcinogenic compounds, a cell having the phenotype of being transformed in the absence of a known carcinogen is used. Such cells have one or more of the transformation characteristics discussed above. Such cells are known to those skilled in the art, and include, for example, BPV DNA transfected C127 cells. Further, such cells can include cells which are tumorigenic in nude mice. Such a cell is contacted with a compound to be evaluated for its effectiveness as an anti-carcinogenic agent. After a suitable incubation period, cell growth is scored for the presence or absence of one or more transformation indicators as noted above.

The absence of a transformation characteristic or a reduction in the incidence of transformation characteristics compared to the rate of occurrence of transformation characteristics in the absence of the compound being tested, is an indication that the compound being tested is effective as an anti-carcinogenic agent.

Carcinogens which can be used in this embodiment of the present invention can be any known carcinogen, such as mezerein, teleocidin, okadaic acid, arsenic and vanadate. Alternatively, carcinogens can be any other known carcinogen or carcinogens identified in the future.

The following examples are provided for the purposes of illustration and are not intended to limit the scope of the present invention.

EXAMPLES

Example 1

The following example describes the transfection of a fibroblast host cell with bovine papilloma virus (BPV-1) to produce a cell line of the present invention.

C3H/10T½ fibroblasts, publicly available from the American Type Culture Collection (ATCC No. CCL-226), were grown in Dulbecco's modified Eagle's medium (Gibco) containing 20 mM HEPES [N-2-hydroxyethylpiperazine-N'-2-ethanesulfonic acid] (Sigma), 60 µg/ml. of penicillin G (Sigma) and 100 µg/ml of streptomycin sulfate (Sigma) and supplemented with 10% fetal calf serum (Gibco). Cells were grown initially in 25 cm$^2$ tissue culture flasks (Nunc), then passaged to 75 cm$^2$ tissue culture flasks at the first passage. Cultures were grown at 37° C. in 3% $CO_2$/95% air. Medium was changed twice weekly. Passage 19 of a culture of C3H/10T½ cells was transfected with the pdBPV-1 (142-6) plasmid (publicly available through the ATCC; ATCC No. 37134), prepared by $CsCl_2$ density gradient centrifugation. The plasmid pdBPV-1 (142-6) contains the complete BPV-1 genome cloned into the plasmid pML2d at the Bam HI site (Sarver, A., et al., ibid.). For each 100 mm$^2$ plate (Nunc), 1.25×10$^5$ C3H/10T½ cells were transfected with pdBPV-1 (142-6) by the calcium phosphate precipitation method (Graham, E. L and Vander Erb, A. J. (1973) "A new technique for the assay of infectivity of human adenovirus 5 DNA." Virol. 52:456–467, incorporated herein by reference in its entirety) using 1.05 µg of plasmid DNA and 27.5 µg of sheared calf thymus DNA (as carrier DNA) for 4 hours followed by glycerol shock for three minutes. Cultures were then incubated overnight in normal medium.

On the following day, transfected cells on 100 mm plates were subcultured at a ratio of 1:17 into 60 mm$^2$ plates (Nunc). Mezerein (Sigma), a non-genotoxic carcinogen, was diluted in dimethylsulfoxide (BDH) to a stock of 0.2 mg/ml, then diluted in medium to the desired concentrations. Mezerein (Sigma) was added at to a final concentration of 0.5 ng/ml to 60 mm$^2$ plates containing transfected cells. Cultures were processed in dim light following addition of mezerein and evaluated for the formation of foci.

Example 2

The following example demonstrates the cloning of a cell line of the present invention.

Cloned cell lines were established from foci in transfected cells exposed to mezerein, as described in Example 1, as follows. Cultures were incubated as in Example 1 in the constant presence of 0.5 ng/ml of mezerein with twice weekly changes of medium. Fifteen days after transfection, when foci were clearly visible (1–2 mm in diameter), cultures were rinsed twice with 0.25% trypsin containing 0.02% EDTA, and the centers of individual foci, well-isolated from other foci, were extirpated into about 10 µl of 0.25% trypsin containing 0.02% EDTA in 25 mm$^2$ dishes (Nunc) using an Eppendorf Pipettman. Foci were vigorously agitated by pipetting for 5 minutes to separate cells, then 2 ml of medium (without mezerein) added. Ten foci were isolated separately in this way.

Cells obtained from trypsinized foci on 25 mm plates were incubated until they reached confluence (3 days), then transferred to 60 mm plates and grown to confluence (7 days) Cells from each clone were harvested and frozen in medium containing 10% DMSO for later testing and subcloning. Frozen clones were thawed and grown to subconfluence in 25 cm$^2$ culture flasks (Nunc). To determine response to mezerein of each clone, 2000 untransfected C3H/10T½ cells, passage 20, were coincubated with 200 cells from the cloned cell lines in medium containing 0.5 ng/ml of mezerein. Control co-cultures of each clone were prepared containing no mezerein. Cultures were prepared in duplicate. Medium was changed twice weekly.

After 21 days of incubation, the cultures were stained with 0.025% methylene blue in 50:50 methanol:water, dried, and the foci were counted. Several clones were identified which produced a higher number of foci in the presence of mezerein than in control cultures. The culture with the greatest difference was labeled as S1 and produced an average of 60 foci per 60 mm$^2$ plate in the presence of mezerein and an average of 21 in the absence of mezerein. To subclone S1, 50 cells were plated, using serial dilutions, on 100 mm$^2$ plates in triplicate. The plates were incubated in normal medium for 8 days, at which time colonies were 2–3 mm in diameter but not in contact with each other. Cultures were rinsed twice with 0.25% trypsin containing 0.02% EDTA, and the centers of individual colonies, well-isolated from other colonies, were extirpated into about 10 µl of 0.25% trypsin containing 0.02% EDTA in 25 mm$^2$ dishes (Nunc) using an Eppendorf Pipettman. Colonies were vigorously agitated by pipetting for 5 minutes to separate cells, then 2 ml of medium was added. Ten colonies were isolated separately in this way. The subclones were grown and passaged into larger flasks, then tested in co-culture assays in the presence and absence of mezerein in the same way as the foci were tested above. The original S1 clone resulted in ten subclones, one of which produced an average of 70 foci in the presence of mezerein and an average of 9 foci in the absence of mezerein. This subclone was designated T1.

Example 3

The following example describes the determination of the genotypic stability of a cell line of the present invention.

For determination of genotypic stability, T1 cells, produced and selected as described above in Examples 1 and 2, were co-cultured as described above with non-transfected C3H/10T½ cells, passages 12–20, in the presence and absence of 0.5 ng/ml of mezerein, 2 µM $VOSO_4 \cdot 2H_2O$ (BDH), or normal medium. T1 cells were passaged in 25 cm$^2$ flasks (Corning) twice weekly at subconfluence. At each passaging, co-cultures were set up in triplicate, and 1 ml of cell suspension was plated on each of two 100 mm plates (Corning) in normal medium for DNA isolation.

Cells were collected from the 100 mm plates at subconfluence by scraping into phosphate buffered saline (PBS). These were centrifuged at 1000 rpm for 5 minutes to pellet the cells, and then the pellets were preserved at −20° C. until used for DNA isolation.

Total nucleic acids from cells collected from each passage were extracted by a modification of the sodium dodecyl sulfate/proteinase K method (Gross-Bellard, M., et al (1973) "Isolation of High Molecular Weight DNA from Mammalian Cells." Eur. J. Biochem. 36, 32–36). Briefly, total nucleic acids were purified by one round of phenol/chloroform extraction and precipitation in ethanol. Prior to addition of buffer saturated phenol containing 0.1% 8-hydroxyquinoline (Sigma), protein was removed by digestion with proteinase K (Sigma). DNA was dissolved in TE buffer and concentrations determined by reading optical density at 260 nm.

Nucleic acids from cell pellets were dissolved in TE buffer to concentrations of 0.4 to 0.8 µg/µl. 3 µl of these nucleic solutions (1–2 µg) were loaded per well on to 0.7% agarose (Biorad) gels and electrophoresed in Tris-Borate-EDTA buffer at 46 V for 4 hours. Gels were stained in ethidium bromide and photographed, and then were capillary transferred by the method of Southern (Southern, E. M. (1975) J. Mol. Biol. 98, 503–517) to nylon membranes (Boehringer Mannheim).

For restriction endonuclease digestion of DNA from cell pellets, 1–3 μg of cellular DNA was digested with Bam HI (Gibco) or Sal I (Gibco) using contemporaneous digestion of pdBPV-1(142-6) DNA standards as controls. Restriction endonuclease digested samples were loaded on 0.7% agarose gels, electrophoresed, stained with ethidium bromide, photographed and blotted as above. Size standards on each gel consisted of HindIII lambda fragments (Gibco).

Nucleic acids immobilized by crosslinking to nylon membranes for 30 minutes at 120° C. were probed using a digoxigenin chemiluminescent system (Boehringer Mannheim). Following the method included with the product, membranes were prehybridized for 6 hours at 42° C. using deionized 50% formamide, 0.1% N-larylsarcosine, 2% blocking buffer (Boehringer Mannheim), 5×SSC and 0.02% SDS in deionized distilled water.

Blots were then hybridized for 20 hours at 42° C. using digoxigenin-labeled pdBPV-1 (142-6) DNA and lambda HindIII fragment DNA as probes in the above hybridization solution. The pdBPV-1(142-6) probe was prepared using the DIG High Prime DNA Labeling Kit II (Boehringer Mannheim). For this method, 2 μg of pdBPV-1 (142-6), was denatured at 100° C. for 10 minutes. 4 μg of DIG-High Primer was added and the mixture incubated for 20 hours at 37° C. The reaction was quenched by heating at 65° C. for 10 minutes and adding EDTA to a final concentration of 0.2M EDTA. Digoxigenin-labeled DNA was quantified using the test strips included in the kit. Digoxigenin-labeled DNA was stored at −20° C. Labeling of lambda HindIII fragments was done in the same way.

Copy number standards for pdBPV-1 (142-6) were made up in calf thymus DNA by assuming a value of one gene copy of BPV DNA equivalent to 14 pg/10 μg of cellular DNA (Watts, S. L., et al (1984) "Cellular Transformation by Human Papillomavirus DNA in vitro." *Science* 225, 634–636). Standards representing 1, 10 and 100 copies per genome were run on the same gels as T1 DNA extracts and blotted and hybridized at the same time.

After hybridization, blots were washed in 2×SSC+0.1% SDS for five minutes at 21° C. This was repeated once. Blots were then washed in 0.1% SSC+0.1% SDS twice for 15 minutes at 68° C. in a hybridization incubator. Blots were transferred to 0.3% Tween 20 solution at 21° C. and washed for 5 minutes. The washing step was repeated once. The blots were then incubated at 21° C. in 1% blocking buffer for 30 minutes. This blocking step was repeated once. 10 ml of Anti-DIG (anti-digoxigenin-AP, Boehringer Mannheim) was added to 100 ml of 1% blocking buffer. The blots were incubated in this buffer at 21° C. for 30 minutes with rocking in a sealed plastic bag. The blots were then washed twice at 21° C. in 0.3% Tween 20 solution for 30 minutes each time, and then rinsed in equilibrating buffer (1% blocking buffer in 2×SSC+0.1% SDS) for 5 minutes.

The blots were then placed in individual plastic folders and 500 ml of CSPD solution (Boehringer Mannheim) added for each blot and spread evenly over the blots. The folders containing the blots were incubated at 37° C. for 15 minutes. The blots, still in the folders, were exposed to X-ray film (Amersham Hyperfilm ECL) in X-ray cassettes at 21° C. for 15 minutes.

Comparison of DNA from fourteen consecutive passages of T1 cells with copy number standards indicated that copy number remained between 100 and 120 copies per genome from passage to passage. There was no significant pattern to variations between passages.

pdBPV-1 (142-6) DNA hybridized to undigested T1 DNA at 23 kb in all passages. Bam HI digestion of T1 DNA, probed with digoxigenin-labeled pdBPV-1 (142-6) produced approximately 5 copies per genome of the expected 2.5 kb fragment corresponding to pML2d and the majority of material hybridizing to a broad smear. This was consistent for all passages. Hybridization of stripped, undigested blots with digoxigenin-labeled pML2d showed the presence of pML2d at 23 kb in undigested T1 DNA. In Bam HI digested T1 DNA, digoxigenin-labeled pML2d hybridized to approximately 5 copies corresponding to pML2d at 2.5 kb and to a large smear. Digestion of T1 DNA with Sal I, normally a single cut enzyme with the site in pML2d, produced only material which hybridized with pdBPV-1 (142-6) at 23 kb. There was no change from undigested T1 DNA. The lack of separation of most of the 2.5 kb fragment by Bam HI digestion of T1 DNA indicates that at least one of the Bam sites is deleted. Lack of digestion by Sal I suggests that the Sal I site is also deleted. Taken together, this indicates that T1 DNA contains pdBPV-1(142-6) integrated randomly in multiple copies at a deletion site which includes the part of pdBPV-1(142-6) around the BamHI and SalI sites. This suggests that part of the E2 ORF has been deleted.

These data indicate that the genotypic nature of the pdBPV-1 (142-6) DNA does not change from passage to passage either in copy number or in state of integration and that deletion of part of the original pdBPV-1 (142-6) plasmid has occurred.

Example 4

The following example describes the determination of the phenotypic stability of a cell line of the present invention.

Phenotypic stability was determined by co-culturing 200 T1 cells of 14 consecutive passages, produced and selected as described in Examples 1 and 2, with 2000 non-transfected C3H/10T½ cells, passages 13–20, as described above in Examples 2 and 3. The response to 0.5 ng/ml of mezerein was determined as outlined in Example 2 above. From passages 28 to 41 (14 passages), the ratio of number of foci in the presence of mezerein to number of foci in the absence of mezerein averaged 2.0 with a standard deviation of 0.8. The variation was not systematic and was due to variation in viability of the C3H/10T½ lawn cells and other chance factors.

Example 5

The following example demonstrates the response of a test cell of the present invention to a set of test carcinogens.

To determine the response of the T1 cell described in the Examples above to a set of test carcinogens and noncarcinogenic controls, dose response curves were developed using co-culturing methods as described above (Examples 3 and 4) with untransformed C3H/10T½ cells to optimize focus formation (in the case of carcinogens). Toxicity levels were determined as the dosages above which focus formation would be decreased from the controls not exposed to carcinogens. This determination of toxicity levels assumes that carcinogen toxicity would inhibit the ability of co-cultures to produce foci and that focus formation would decrease above this level, a phenomenon which was observed in all cases. This level was also an indication of toxicity of noncarcinogenic controls (e.g., caffeine and arsenate). Cultures were exposed to dosages of noncarcinogenic controls up to toxic levels to determine whether increasing toxicity might cause an enhancement in numbers of foci.

To develop dose response curves, all cultures were incubated for 21 days with continuous presence of test chemicals and medium changes twice weekly. Cultures incubated in normal medium contained no additional compounds. For noncarcinogenic controls, caffeine-treated cultures received 50, 100, 150 or 300 mg/ml of caffeine (Sigma, anhydrous, reference grade). Tetrahydrofuran (BDH, non-stabilized)-treated cultures received only one dose at 0.1%. Arsenate (BDH) as $Na_2HAsO_4 \cdot 7H_2O$ was provided to cultures at dosages of 5, 10 and 20 $\mu$M.

Carcinogen-exposed cultures were exposed to mezerein (Sigma) at 0.1, 0.5, 1.0, 2.0 and 5.0 ng/ml; diethylstilbestroel (Sigma, practical grade) at 0.1, 0.5, 1.0 or 5.0 $\mu$M; 20-methylcholanthrene (Sigma) at 0.5, 1.0, 5.0 or 10.0 $\mu$M; benzo[a]pyrene (Sigma) at 0.033, 0.33, 1.0, or 3.3 $\mu$M; vanadyl as $VOSO_4 \cdot 2H_2O$ (BDH) at 0.001, 0.01, 0.1, 1.0 or 2.0 $\mu$M; 1-methyl-3-nitro-1-nitrosoguanidine (Sigma) at 0.05, 0.1, 0.5 or 1.0 $\mu$M; cadmium as $CdCl_2$ (Sigma) at 0.01, 0.1, 1 or 5 $\mu$M; or arsenite (Sigma) as $NaAsO_2$ at 0.01, 0.1, 1.0 or 2.0 $\mu$M. Diethylstilbestroel, 20-methylcholanthrene, 1-methyl-3-nitro-1-nitrosoguanidine or benzo[a]pyrene were made up as stock solutions in fresh tetrahydrofuran, kept frozen, then diluted to the final concentration using medium. $Na_2HAsO_4 \cdot 7H_2O$ was made up fresh weekly as a 200 $\mu$M stock solution in deionized distilled water and kept frozen. Caffeine was made up as a stock solution of 15 mg/ml in deionized distilled water and kept frozen. Mezerein was made up in a stock solution in dimethylsulfoxide as noted elsewhere and kept frozen. $VOSO_4 \cdot 2H_2O$, $CdCl_2$, $Fe(III)Cl_3$ or $NaAsO_2$ were made up fresh in deionized distilled water for each medium change. Table 1 shows the numbers of foci formed in these reconstruction assays by cell cultures exposed to non-carcinogens and carcinogens.

The results shown in Table 1 indicate that the cell line, T1, responds to selected polyaromatic hydrocarbons, nitrosamines, nongenotoxic carcinogens, and carcinogenic metal salts with approximately a 20% increase in numbers of foci. Noncarcinogenic compounds do not increase numbers of foci. In the case of 20-methylcholanthrene, it was not possible to determine the response, because at all concentrations, very few cells remained on the plates, suggesting that the 20-methylcholantrene was very toxic to cells. This toxicity may have been due to generation of peroxides and active oxygen-free radicals by a reaction with peroxides contaminating the solvent tetrahydrofuran. Enhanced transformation in cultures exposed to the non-genotoxic metal salt, $Fe(III)Cl_3$, may have occurred by a similar mechanism since $Fe^{+3}$ may be redox active. This result indicates that potentially redox active compounds may produce inaccurate results if conditions exist to facilitate redox activity.

In summary, the foregoing examples describe a cell line, denoted T1, which has the following characteristics: (1) it is genetically stable from passage to passage over at least 14 passages; (2) it is phenotypically stable in its response to a test carcinogen; (3) it has a deletion of part of the BPV-1 E2 ORF; and, (4) it undergoes increased transformation in response to nongenotoxic carcinogens and genotoxic carcinogens by producing increased numbers of transformed foci as measured using a lawn of contact inhibited, untransformed C3H/10T½ cells.

TABLE 1

| Chemical | Optimal Dose | #Foci In Controls | #Foci In Treated Cells | Ratio of Treated: Untreated Foci | Chemical Class |
| --- | --- | --- | --- | --- | --- |
| Noncarcinogenic controls | | | | | |
| caffeine | 150 mg/ml | 64 + 1 | 64 + 3 | 1 | alkaloid |
| tetrahydrofuran | 0.1% | 69 + 11 | 70 + 7 | 1 | heterocycle |
| $FeCl_3$ | 50 $\mu$M | 64 + 1 | 77 + 5 | 1.2 | metal salt |
| arsenate | 5 $\mu$M | 95 + 5 | 91 + 5 | 1 | metal salt |
| Carcinogens | | | | | |
| Mezerein | 2.0 ng/ml | 72 + 5 | 143 + 18 | 2 | promoter |
| Vanadyl | 0.1 $\mu$M | 60 + 3 | 79 + 8 | 1.3 | metal salt |
| Arsenite | 0.01 $\mu$M | 63 + 1 | 75 + 2 | 1.2 | metal salt |
| Cadmium | 1.0 $\mu$M | 70 + 5 | 100 + 7 | 1.4 | metal salt |
| Diethylstilbestroel | 0.5 $\mu$M | 74 + 2 | 83 + 4 | 1.12 | steroid |
| 1-methyl-3-nitro-1-nitrosoguanidine | 0.1 $\mu$g/ml | 74 + 2 | 81 + 4 | 1.1 | nitrosamine |
| 20-methylcholanthrene | nil | nil | nil | N/A | polyaromatic hydrocarbon |
| Benzo[a]pyrene | 0.033 $\mu$M | 78 + 2 | 90 + 6 | 1.15 | polyaromatic |

The foregoing discussion of the invention has been presented for purposes of illustration and description. Further, the description is not intended to limit the invention to the form disclosed herein. Consequently, variation and modification commensurate with the above teachings, within the skill and knowledge of the relevant art, are within the scope of the present invention. The embodiment described hereinabove is further intended to explain the best mode presently known of practicing the invention and to enable other skilled in the art to utilize the invention as such, or other embodiments, and with the various modifications required by their particular application or uses of the invention. It is intended that the appended claims be construed to include alternative embodiments to the extent permitted by the prior art.

What is claimed is:

1. A test cell transfected with a recombinant nucleic acid molecule from a bovine papilloma virus (BPV), wherein said recombinant nucleic acid molecule does not include a nucleic acid sequence encoding viral proteins that cause:

(a) a variation in said test cell's phenotypic transformation response to a carcinogen;

(b) instability of viral integration;

(c) variation of nucleic acid copy number; or (d) variation or reduction in the ability of said test cell to be transformed by a carcinogen; and, wherein said test cell has been selected in the presence of a carcinogen to be less transformed prior to contact with said carcinogen than after contact with said carcinogen.

2. The test cell of claim 1, wherein said test cell maintains a copy number of said recombinant nucleic acid molecule within at cast about 50% of an original copy number present before a first passage of said test cell.

3. The test cell of claim 1, wherein said bovine papilloma virus is selected from the group consisting of bovine papilloma virus type 1 and bovine papilloma virus type 4.

4. The test cell of claim 1, wherein said recombinant nucleic acid molecule comprises an open reading frame selected from the group consisting of the BPV E5, E6 and E7 open reading frames.

5. The test cell of claim 1, wherein said recombinant nucleic acid molecule comprises a BPV E5 open reading frame.

6. The test cell of claim 1, wherein said recombinant nucleic acid molecule is a BPV genome in which an open reading frame selected from the group consisting of E1 and E2 open reading frames has been modified such that said open reading frame is deleted or does not encode a protein that causes:

(a) a variation in said test cell's phenotypic transformation response to a carcinogen;

(b) instability of viral integration;

(c) variation of nucleic acid copy number; or (d) variation or reduction in the ability of said test cell to be transformed by a carcinogen.

7. The test cell of claim 1, wherein said test cell is transfected with plasmid pdBPV-1 having nucleotides within the E2 open reading frame deleted such that said open reading frame does not encode a protein that causes:

(a) a variation in said test cell's phenotypic transformation response to a carcinogen;

(b) instability of viral integration;

(c) variation of nucleic acid copy number; or (d) variation or reduction in the ability of said test cell to be transformed by a carcinogen.

8. The test cell of claim 1, wherein said test cell is mammalian.

9. The test cell of claim 1, wherein said test cell is selected from the group consisting of fibroblasts, keratinocytes, established fibroblast cell lines, and established epithelial cell lines.

10. The test cell of claim 1, wherein said test cell is selected from the group consisting of mouse C127 cells, C3H/10T½ cells, human newborn foreskin keratinocytes, and primary fibroblast cultures of C57BL/6J mice.

11. The test cell of claim 1, wherein said test cell has been selected in the presence of mezerein.

12. A test cell, comprising a mammalian cell transfected with a recombinant nucleic acid molecule encoding a bovine papilloma virus (BPV) genome in which an open reading frame selected from the group consisting of E1 and E2 open reading frames has been modified such that said open reading frame is deleted or does not encode a protein that causes:

(a) a variation in said test cell's phenotypic transformation response to a carcinogen;

(b) instability of viral integration;

(c) variation of nucleic acid copy number; or (d) variation or reduction in the ability of said test cell to be transformed by a carcinogen;
wherein said test cell has been selected in the presence of a carcinogen to be less transformed prior to contact with said carcinogen than after contact with said carcinogen; and,
wherein said test cell maintains a stable copy number of said recombinant nucleic acid molecule over at least about 5 passages of said test cell.

13. A test cell, comprising a fibroblast cell transfected with plasmid pdBPV-1 having nucleotides within the E2 open reading frame deleted such that said open reading frame does not encode a protein that causes:

(a) a variation in said test cell's phenotypic transformation response to a carcinogen;

(b) instability of viral integration;

(c) variation of nucleic acid copy number; or (d) variation or reduction in the ability of said test cell to be transformed by a carcinogen;
wherein said test cell has been selected in the presence of a carcinogen to be less transformed prior to contact with said carcinogen than after contact with said carcinogen; and,
wherein said test cell maintains a copy number of said recombinant nucleic acid molecule within at least about 50% of an original copy number present before a first passage of said test cell.

* * * * *

UNITED STATES PATENT AND TRADEMARK OFFICE
CERTIFICATE OF CORRECTION

| | |
|---|---|
| PATENT NO. | : 6,153,429 |
| DATED | : November 28, 2000 |
| INVENTOR(S) | : Kowalski |

It is certified that error appears in the above-identified patent and that said Letters Patent is hereby corrected as shown below:

<u>Title page,</u>
After "[22] Filed:", delete October 16, 1997, and insert -- October 15, 1997 -- therefor.

Signed and Sealed this

Twenty-fifth Day of September, 2001

Attest:

NICHOLAS P. GODICI
*Acting Director of the United States Patent and Trademark Office*

*Attesting Officer*